US008152854B2

(12) United States Patent
Imbriglia et al.

(10) Patent No.: US 8,152,854 B2
(45) Date of Patent: Apr. 10, 2012

(54) RESURFACING IMPLANT FOR THE WRIST AND METHOD OF IMPLANTATION THEREOF

(76) Inventors: Joseph E. Imbriglia, Wexford, PA (US); Alexander Anzarut, Victoria (CA)

( * ) Notice: Subject to any disclaimer, the term of this patent is extended or adjusted under 35 U.S.C. 154(b) by 19 days.

(21) Appl. No.: 12/570,586

(22) Filed: Sep. 30, 2009

(65) Prior Publication Data
US 2011/0077744 A1 Mar. 31, 2011

(51) Int. Cl.
*A61F 2/42* (2006.01)
(52) U.S. Cl. .................................. 623/21.12; 623/21.14
(58) Field of Classification Search ............... 623/21.11, 623/21.12, 21.14, 23.43, 23.44
See application file for complete search history.

(56) References Cited

U.S. PATENT DOCUMENTS

| 3,879,767 | A | 4/1975 | Stubstad |
|---|---|---|---|
| 4,003,096 | A | 1/1977 | Frey |
| 4,040,130 | A | 8/1977 | Laure |
| 4,063,314 | A | 12/1977 | Loda |
| 4,106,128 | A | 8/1978 | Greenwald et al. |
| 4,178,640 | A | 12/1979 | Buechler et al. |
| 4,180,871 | A | 1/1980 | Hamas |
| 4,198,712 | A | 4/1980 | Swanson |
| 4,229,840 | A | 10/1980 | Gristina |
| 4,229,841 | A | 10/1980 | Youm et al. |
| 4,259,752 | A | 4/1981 | Taleisnik |
| 4,307,473 | A | 12/1981 | Weber |
| 4,645,505 | A | 2/1987 | Swanson |
| 4,714,476 | A | 12/1987 | Ranawat et al. |
| 4,784,661 | A | 11/1988 | Beckenbaugh et al. |
| 4,936,854 | A | 6/1990 | Swanson |
| 4,936,860 | A | 6/1990 | Swanson |
| 4,955,915 | A | 9/1990 | Swanson |
| 4,969,908 | A | 11/1990 | Swanson |
| 5,108,444 | A | 4/1992 | Branemark |
| 5,133,762 | A | 7/1992 | Branemark |
| 5,314,485 | A | 5/1994 | Judet |
| 5,326,364 | A | 7/1994 | Clift, Jr. et al. |
| 5,458,646 | A | 10/1995 | Giachino et al. |
| 5,507,821 | A | 4/1996 | Sennwald et al. |
| 5,683,466 | A | 11/1997 | Vitale |
| 5,702,470 | A | 12/1997 | Menon |
| 5,743,918 | A | 4/1998 | Calandruccio et al. |
| 5,766,258 | A | 6/1998 | Simmen |
| 5,888,203 | A | 3/1999 | Goldberg |
| 5,938,699 | A | 8/1999 | Campbell |
| 6,059,832 | A | 5/2000 | Menon |
| 6,090,145 | A | 7/2000 | Hassler et al. |
| 6,284,001 | B1 | 9/2001 | Knapp |
| 6,302,915 | B1 | 10/2001 | Cooney, III et al. |
| 6,383,223 | B1 | 5/2002 | Baehler et al. |
| 6,436,146 | B1 | 8/2002 | Hassler et al. |

(Continued)

*Primary Examiner* — David Isabella
*Assistant Examiner* — Brian Dukert
(74) *Attorney, Agent, or Firm* — The Webb Law Firm (57) ABSTRACT

A modular resurfacing implant for a radioscaphoid joint of a wrist includes a stem and an articular component coupled to the stem. The stem includes a threaded body for implantation into a distal radius and a connection member positioned at a second end of the stem. The articular component includes a body member configured to resurface a scaphoid fossa of the distal radius. The body member includes a concave top surface matching a curvature of the scaphoid fossa and a bottom surface having a post extending therefrom that is configured to mate with the connection member of the stem. The articular component is configured to resurface the scaphoid fossa while leaving a lunate fossa of the distal radius intact.

19 Claims, 5 Drawing Sheets

U.S. PATENT DOCUMENTS

| | | |
|---|---|---|
| 6,485,520 B1 | 11/2002 | Hubach et al. |
| 6,652,587 B2 | 11/2003 | Felt et al. |
| 6,746,486 B1 | 6/2004 | Shultz et al. |
| 6,814,757 B2 | 11/2004 | Kopylov et al. |
| 6,827,741 B2 | 12/2004 | Reeder |
| 6,890,358 B2 | 5/2005 | Ball et al. |
| 6,969,407 B2 | 11/2005 | Klotz et al. |
| 7,160,331 B2 | 1/2007 | Cooney, III et al. |
| 7,320,709 B2 | 1/2008 | Felt et al. |
| 2003/0187511 A1 | 10/2003 | Ball et al. |
| 2004/0073316 A1 | 4/2004 | Guerard et al. |
| 2004/0117025 A1 | 6/2004 | Reindel |
| 2004/0230312 A1 | 11/2004 | Hanson et al. |
| 2005/0004675 A1 | 1/2005 | Shultz et al. |
| 2005/0085921 A1 | 4/2005 | Gupta et al. |
| 2005/0171613 A1 | 8/2005 | Sartorius et al. |
| 2005/0216090 A1* | 9/2005 | O'Driscoll et al. ........ 623/20.32 |
| 2005/0247319 A1 | 11/2005 | Berger |
| 2006/0004462 A1 | 1/2006 | Gupta |
| 2006/0009853 A1 | 1/2006 | Justin et al. |
| 2006/0009854 A1 | 1/2006 | Justin et al. |
| 2006/0009855 A1 | 1/2006 | Goble et al. |
| 2006/0030946 A1 | 2/2006 | Ball et al. |
| 2006/0036330 A1 | 2/2006 | Shultz et al. |
| 2006/0287730 A1 | 12/2006 | Segal et al. |
| 2007/0055381 A1 | 3/2007 | Berelsman et al. |
| 2007/0078518 A1 | 4/2007 | Lavi |
| 2007/0142919 A1 | 6/2007 | Cooney, III et al. |
| 2007/0185582 A1 | 8/2007 | Palmer et al. |
| 2007/0198095 A1 | 8/2007 | VanDer Meulen et al. |
| 2007/0225820 A1 | 9/2007 | Thomas et al. |
| 2007/0288029 A1 | 12/2007 | Justin et al. |
| 2008/0027558 A1 | 1/2008 | Palmer et al. |
| 2008/0051909 A1 | 2/2008 | Wolfe et al. |
| 2008/0154384 A1 | 6/2008 | Acker et al. |
| 2009/0018560 A1 | 1/2009 | Mayer et al. |

* cited by examiner

RESURFACING IMPLANT FOR THE WRIST AND METHOD OF IMPLANTATION THEREOF

BACKGROUND OF THE INVENTION

1. Field of the Invention

The present invention generally relates to orthopedic implants and, more particularly, to a resurfacing implant for the radioscaphoid joint.

2. Description of Related Art

Osteoarthritis (OA), also known as degenerative arthritis, is a type of arthritis caused by the breakdown and eventual loss of articular cartilage. Cartilage normally serves as a "cushion" between the bones of a joint. Loss of this cartilage cushion causes friction between bones, leading to pain and limitation of joint mobility. OA is the most common form of arthritis and affects over 20 million people in the United States. It commonly affects the hands as well as large weight-bearing joints, such as the hips and knees. The most common type of OA at the wrist joint is periscaphoid OA. This is OA between the proximal scaphoid and the scaphoid fossa of the radius.

Periscaphoid OA can be primary or secondary. Primary OA is usually related to the wear and tear associated with aging. Secondary OA is usually due either to a) injury to the scaphoid bone or b) injury to the scapholunate ligament which attaches the scaphoid to the lunate. The most common symptom of OA is pain at the affected joint. In severe OA, complete loss of cartilage causes friction between bones, leading to pain with motion and at rest. Eventually patients also lose mobility at the affected joint.

Various treatments are currently available for treating periscaphoid OA. One option for treatment is surgery to repair the wrist joint. Such surgical treatments are generally reserved for those patients with OA that are particularly severe and unresponsive to conservative treatments. The two most common surgical treatments for periscaphoid OA are 4-corner fusion (4-CF) and proximal row carpectomy (PRC). Unfortunately both of these procedures lead to loss of wrist motion. Another surgical option is a total wrist fusion. However, a total wrist fusion leads to a complete loss of wrist motion.

Alternative treatment options include wrist arthroplasty or joint replacement. However, current wrist arthroplasty technology has significant limitations. Current total joint replacement implants for the wrist require removing large sections of bone and soft tissues due to the large size of the implants. Current implants also require bone purchase or bone cement for stability. Further, implantation of current wrist implants requires making large incisions in the patient to provide the surgeon with the access required to ensure proper alignment of the implants.

Consequently, patients can experience long operating room times, lengthy recovery, and reduced mobility. Revision surgeries are challenging because substantial bone has been removed, and there may not be a salvage procedure other than fusion of the joint. Partial wrist replacements are available; however, such techniques still require bone removal and lead to soft tissue damage during surgery, leading to joint instability and few revision options.

Accordingly, attempts have been made to develop devices to resurface the distal radius of the wrist. For instance, United States Patent Application Publication No. 2007/0185582 to Palmer et al. discloses a radial implant (100A) for the radius (1) of the wrist. The radial implant (100A) has tapered edges to prevent sharp contact with soft tissue and an articulating surface (102A). The articulating surface (102A) has at least one generally concave surface facing the joint space (5), and can have one or more points of concavity generally shaped and oriented to match the scaphoid bone (2) and the lunate bone (3). The radial implant (100A) also includes a static surface (101A) configured to contact the cartilage, bone, or tissue of the radius (1), and is shaped to generally fit within the radius (1). A stabilizing fin (150A) may also be provided, and can be a fixed component of the radial implant (100A) or a separate attachment connected during assembly of the implant (100A). However, such resurfacing implants still suffer from various deficiencies. Since these resurfacing implants are provided as a single integral piece, a relatively large incision still needs to be made for implantation. In addition, such implants also require the resurfacing of the entire distal radius, even if a portion of the distal radius is still healthy.

Accordingly, a need exists for a resurfacing implant for treatment of periscaphoid OA that is provided in two or more modular components. In addition, a further need exists for a resurfacing implant for the wrist that would resurface the scaphoid fossa of the radius while leaving the lunate fossa of the radius, the distal radioulnar joint, and the ulnocarpal joint intact.

SUMMARY OF THE INVENTION

An object of the present invention is to provide a resurfacing implant for treatment of periscaphoid OA that is provided in two or more modular components. An additional object of the present invention is to provide a resurfacing implant for the wrist that would resurface the scaphoid fossa of the radius while leaving the lunate fossa of the radius, the distal radioulnar joint, and the ulnocarpal joint intact.

Accordingly, provided is a modular resurfacing implant for a radioscaphoid joint of a wrist. The implant includes a stem and an articular component coupled to the stem. The stem includes a threaded body for implantation into a distal radius and a connection member positioned at a second end of the stem. The articular component includes a body member configured to resurface a scaphoid fossa of the distal radius. The body member includes a concave top surface matching a curvature of the scaphoid fossa and a bottom surface having a post extending therefrom that is configured to mate with the connection member of the stem. The articular component is configured to resurface the scaphoid fossa while leaving a lunate fossa of the distal radius intact.

The articular component may be positioned such that it forms a smooth surface with the lunate fossa. The top surface of the articular component may be manufactured from a cobalt chrome alloy. The bottom surface of the articular component may be manufactured from titanium.

The connection member of the stem may include a hole configured to mate with the post of the articular component, thereby fixedly coupling the articular component to the stem. The stem may be cannulated. The threaded body of the stem may taper from the second end to a first end. The stem may be manufactured from titanium.

Also provided is a resurfacing implant for a radioscaphoid joint of a wrist. The implant includes a stem having an elongated body with a first end and a second end; and an articular component having a body member extending from the second end of the elongated body of the stem. The elongated body is configured to be implanted into a distal radius of the wrist such that the articular component resurfaces the scaphoid fossa while leaving a lunate fossa of the distal radius intact.

The stem and the articular component may be integrally formed or removably coupled. The elongated body of the stem may be implanted into the distal radius by press fitting the elongated body into an opening formed in the distal radius. Alternatively, the elongated body of the stem may be threaded such that it is threadedly coupled to the distal radius.

The articular component may be positioned such that it forms a smooth surface with the lunate fossa. The articular component may include a concave top surface matching a curvature of the scaphoid fossa and a bottom surface. The top surface may be manufactured from a cobalt chrome alloy. The bottom surface may be manufactured from titanium. The stem may be cannulated. The elongated body of the stem may taper from the second end to the first end.

In addition, provided is a method of resurfacing a radioscaphoid joint of a wrist. The method includes providing a resurfacing implant. The resurfacing implant includes a stem having an elongated body with a first end and a second end; and an articular component having a body member configured to be coupled to the second end of the elongated body of the stem. The method also includes the steps of: making a longitudinal midline wrist incision; implanting the stem in a distal radius of the wrist; removing a diseased portion of bone at a scaphoid fossa of the distal radius; and coupling the articular component to the second end of the elongated body of the stem such that the articular component resurfaces the scaphoid fossa while leaving a lunate fossa of the distal radius intact.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

DETAILED DESCRIPTION OF THE PRESENT INVENTION

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Figure 1:
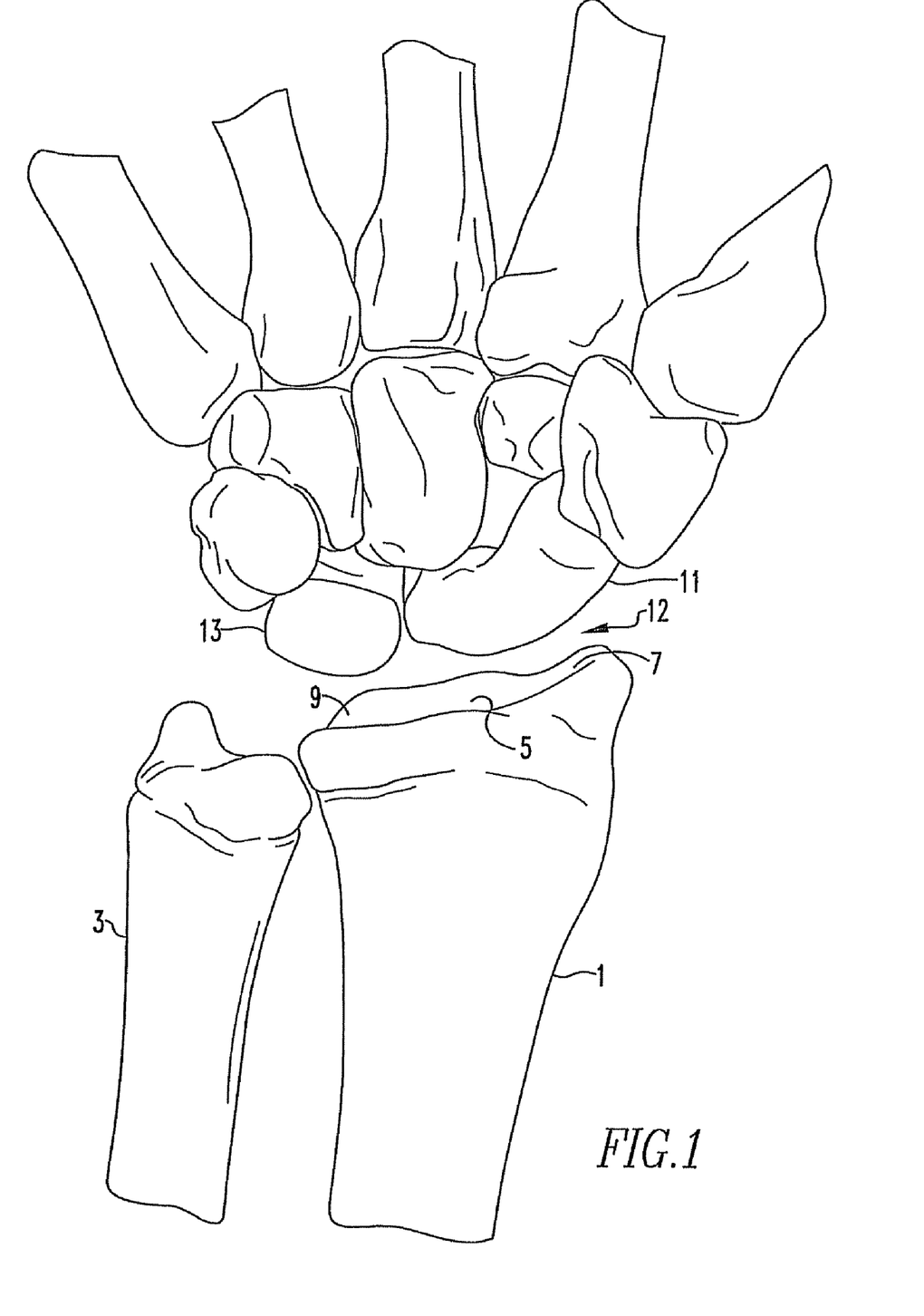
FIG. 1 illustrates bones of a typical human wrist.

FIG. 1 illustrates the primary bones of a human forearm and wrist. The bones of the forearm include a radius 1 and an ulna 3. The radius 1 includes a distal end or distal radius 5 that includes two concavities: the scaphoid fossa 7 and the lunate fossa 9. The scaphoid fossa 7 articulates against a scaphoid bone 11. The radioscaphoid joint 12 is formed where the distal radius 5 articulates with the scaphoid bone 11. The lunate fossa 9 articulates against a lunate bone 13.

With reference to FIGS. 2-5, the present invention is directed to a modular unicompartmental resurfacing hemiarthroplasty system for treatment of periscarphoid OA. The system of the present invention is intended to replace the worn cartilage surface at the scaphoid fossa 7 of the radius 1. Accordingly, the system of the present invention desirably includes: 1) a resurfacing or articular component specific to the scaphoid fossa of the radius; 2) modularity between the articular component and a stem of the implant; and 3) a stem with a screw-fit design.

A modular resurfacing implant 15 for a radioscaphoid joint of a wrist in accordance with one embodiment of the present invention includes a stem 17 and an articular component 19 coupled to stem 17. Stem 17 includes a body 21 for implantation into scaphoid fossa 7 region of distal radius 5. Body 21 includes a first end 23 and a second end 25. Desirably, body 21 tapers from second end 25 to first end 23. A connection member 27 is positioned at second end 25 of stem 17.

Figure 2:
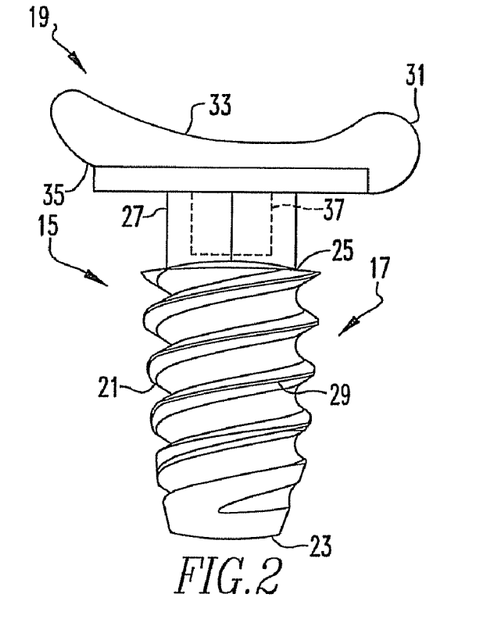
FIG. 2 is a front plan view of a modular resurfacing implant in accordance with one embodiment of the present invention.
Figure 3:
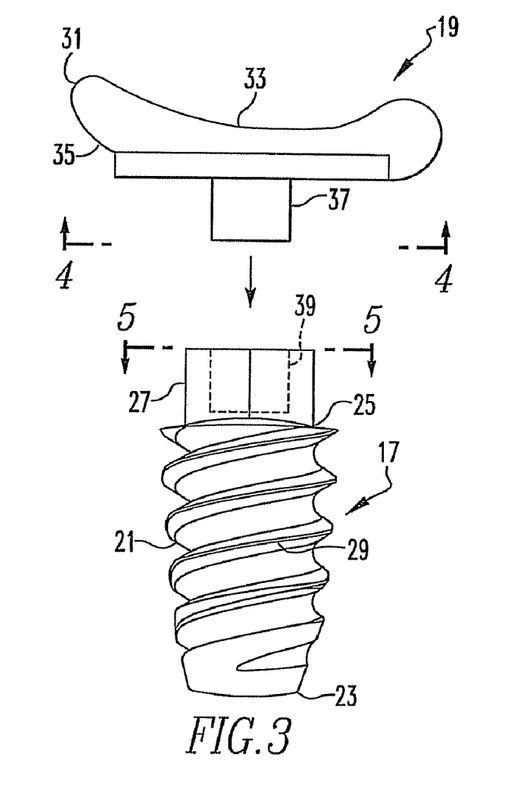
FIG. 3 is an exploded view of the modular resurfacing implant of FIG. 2.

In addition, body 21 desirably includes a plurality of threads 29. Currently, most wrist implants are manufactured to have stems with a press-fit design. A press-fit design requires the implant stem to sit in the center of a medullary canal of radius 1. Accordingly, press-fit stems lead to increased trauma at the medullary canal of radius 1 and increased difficulty with implant removal. In addition, the placement of subsequent implants is difficult because the subsequent implant would require a longer stem. The advantage of providing body 21 of implant 15 of the present invention is that screwing body 21 into the appropriate position leads to minimal damage to the medullary canal in comparison with press-fit stems. Furthermore, replacement of implant 15 with a total wrist implant would be much simpler in patients who have previously had an implant with stem 17 having body 21 with a plurality of threads 29.

Figure 5:
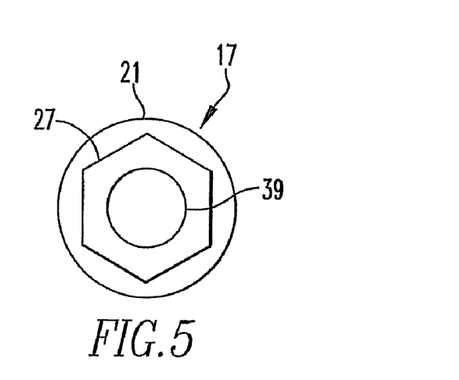
FIG. 5 is a top plan view of a stem of the modular resurfacing implant of FIG. 2.

Stem 17 is provided in a variety of widths and lengths, thereby allowing surgeons to accommodate the various types of patient bone size and density. Desirably, stem 17 is manufactured from titanium with a roughened surface to encourage osseointegration. Finally, stem 17 is cannulated to allow the surgeon to pass stem 17 over previously placed guide wire, such as a Kirshner wire. This allows the surgeon to check and optimize the placement of the Kirshner wire. Once the position of the Kirshner wire is confirmed, stem 17 can be positioned in scaphoid fossa 7 of distal radius 5 using the Kirshner wire as a guide.

Articular component 19 includes a body member 31 configured to resurface scaphoid fossa 7 of distal radius 5. Body member 31 includes a generally concave top surface 33 matching a curvature of scaphoid fossa 7 and a bottom surface 35 having a post 37 extending therefrom that is configured to mate with a hole 39 provided in connection member 27 of body 21 of stem 17. Accordingly, articular component 19 is fixedly coupled to stem 17 when post 37 is frictionally fit within hole 39 by a Morse Taper-Cold Weld fit. In operation, as will be described in greater detail hereinafter, stem 17 is implanted into a patient's distal radius 5 and, thereafter, articular component 19 is connected thereto as described hereinabove. There are numerous advantages of such an implant 15 having such a modular design. For instance, the sizes of stem 17 and articular component 19 can be independently adjusted according to the patient's unique anatomy and size. In addition, a modular design allows the surgeon to implant the device with less trauma and disruption to the wrist ligaments. The smaller modular components can be inserted with a smaller exposure than large single component implants. By using a smaller exposure, fewer wrist ligaments are disrupted, which leads to a shorter recovery and a more stable wrist.

Figure 7:
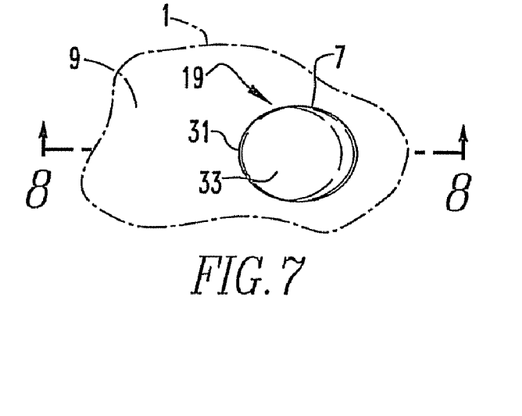
FIG. 7 is a top plan view of the radius of a typical human wrist with the modular resurfacing implant of FIG. 2 implanted therein.

Body member 31 of articular component 19 is sized and shaped to replace only the damaged scaphoid fossa 7 while leaving a lunate fossa 9 of distal radius 5, the distal radioulnar joint, and the ulnocarpal joint intact. Body member 31 may be circular, elliptical (as shown in FIG. 7) or any other suitable shape to replace scaphoid fossa 7. Accordingly, minimal cartilage and bone needs to be removed from the surface of distal radius 5. Therefore, implant 15 is desirably used for the treatment of periscaphoid OA. As described hereinabove, periscaphoid OA is a specific type of arthritis which affects scaphoid fossa 7, but not lunate fossa 9 of distal radius 5. Standard surgical treatment for periscaphoid OA requires an intact lunate fossa 9 at distal radius 5 in order for the surgical treatment to be successful. Currently available implants replace both the scaphoid fossa 7 and lunate fossa 9 of distal radius 5. As a result, these implants do not allow for patients to undergo standard surgical treatments for periscaphoid OA if the implant should fail. In addition, the implantation of currently available implants requires removal of significantly more bone, cartilage, and ligaments than the implantation of implant 15. As a result, patients with failed implants often cannot undergo a second implant surgery. If patients have a problem with the implant, their main option becomes a total wrist fusion. Unfortunately, the current implants also make total wrist fusion more difficult to achieve because of the large amount of bone that is removed.

Implant 15 of the present invention is designed to leave lunate fossa 9 of distal radius 5 intact. This allows patients to undergo standard periscaphoid surgical treatment at a later date if the patient rejects the implant or if the implant fails. Furthermore, implant 15 is designed to only resurface scaphoid fossa 7. Unlike currently available implants that remove a thick portion of bone from distal radius 5, implant 15 only requires the removal of a small portion of cartilage/bone from distal radius 5. This advantageously allows a patient to undergo treatment at a later time with a standard implant or complete wrist fusion if implant 15 is unsuccessful in treating the periscaphoid OA. Finally, the ligaments of the wrist are maintained during the implantation of implant 15 providing patients with improved stability in the wrist.

Figure 4:
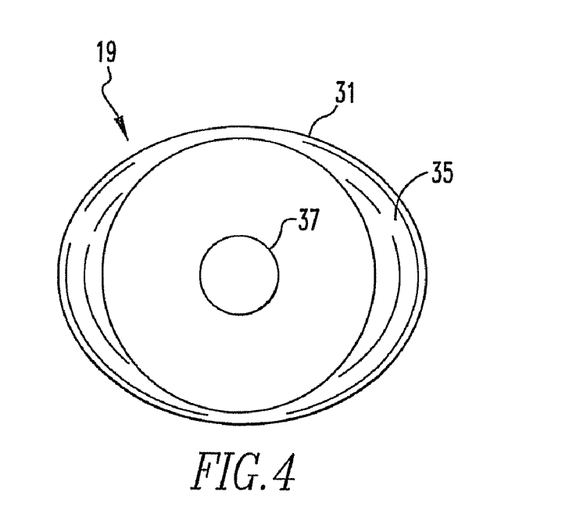
FIG. 4 is a bottom plan view of an articular component of the modular resurfacing implant of FIG. 2.

A standard articular component 19 has a height of approximately 13 mm and a width of approximately 15 mm. However, this is not to be construed as limiting the present invention, as the articular component 19 is envisioned as being available in a variety of sizes (i.e., heights and widths) to match the needs of various patients. Top surface 33 of articular component 19 is desirably surfaced with a soft metal, such as a cobalt chrome alloy. Bottom surface 35 of articular component 19 may be manufactured from titanium with a roughened surface to encourage osseointegration.

Figure 6:
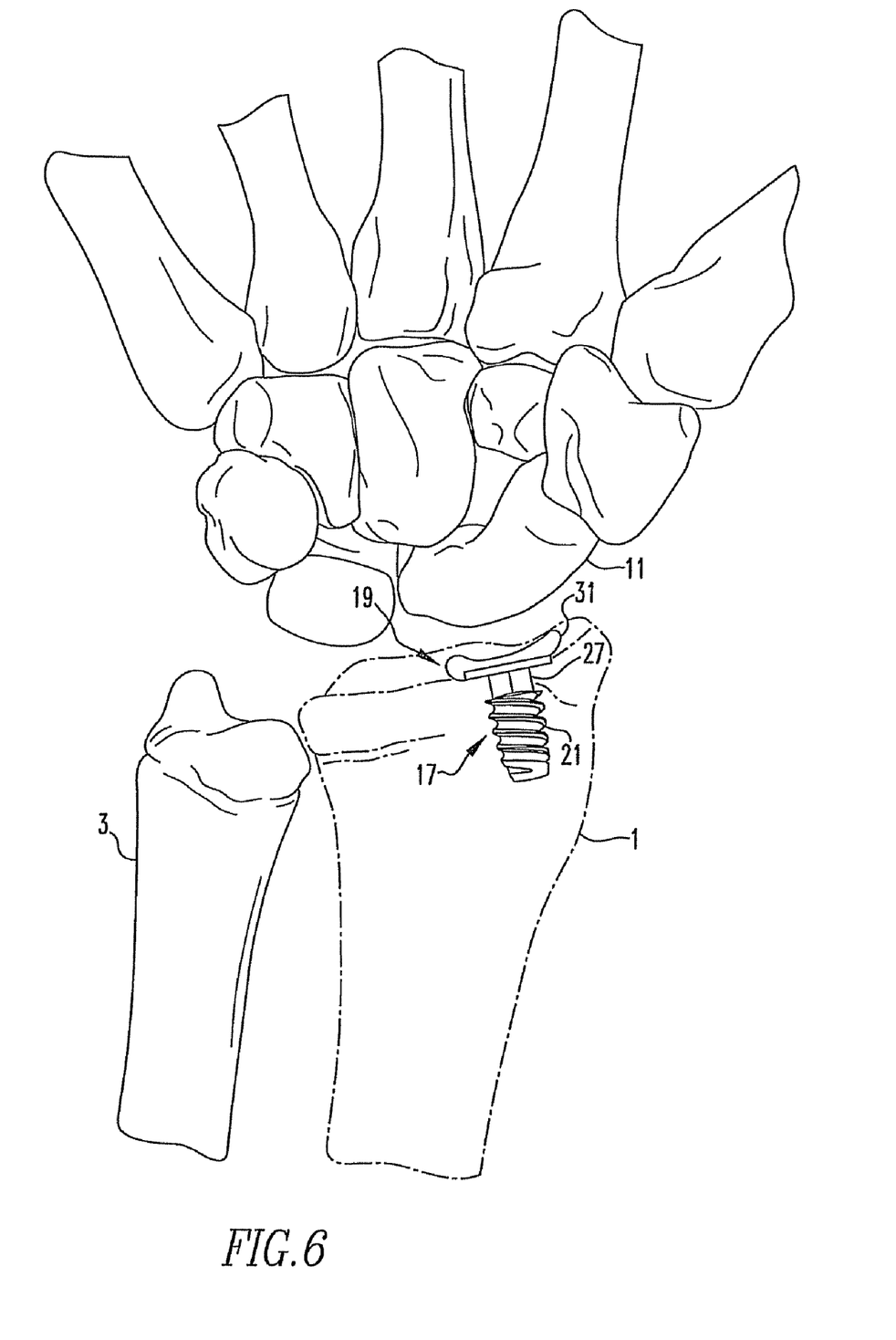
FIG. 6 is a front view of the bones of a typical human wrist with the modular resurfacing implant of FIG. 2 implanted therein.
Figure 8:
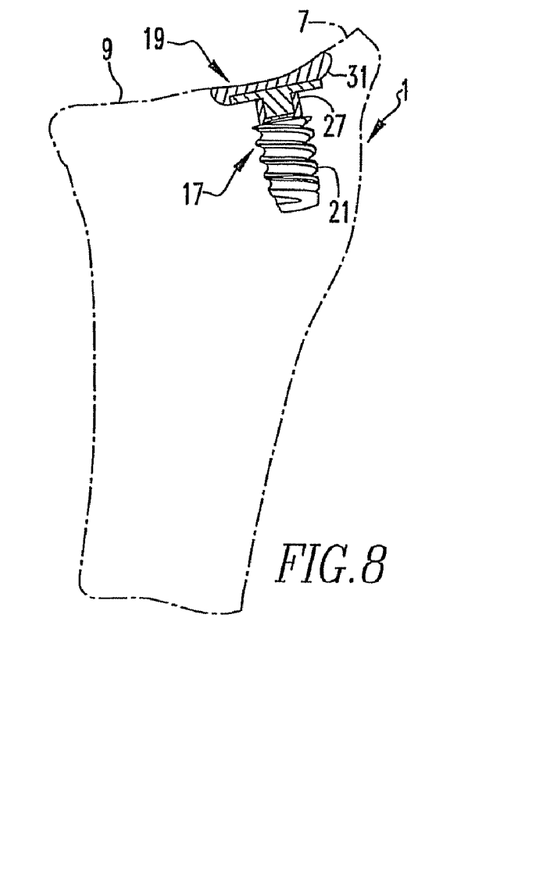
FIG. 8 is a cross-sectional view of the human wrist with the modular resurfacing implant implanted therein of FIG. 7 taken along line 8-8.

With reference to FIGS. 6-8 and with continued reference to FIGS. 1-5, the procedure for implanting implant 15 is as follows. First, a single longitudinal midline wrist incision is made down to the level of the extensor retinaculum. The third and second extensor compartments are opened and their tendons are retracted radially. The fourth compartment is opened and its tendons are retracted ulnarly. The posterior interosseous nerve is identified and resected. Either a T-incision of the capsule or ulnar based capsular flap is then made.

Thereafter, the articular surfaces of scaphoid 11 and scaphoid fossa 7 are examined to assess for OA. A flexible guide wire, such as a Kirshner wire, is placed into distal radius 5. A guide is used to ensure the wire passes through radius 1 parallel to a shaft of radius 1. The guide also assists to ensure the entry point is at the center of scaphoid fossa 7. Stem 17 is then placed over the Kirshner wire such that the Kirshner wire enters through first end 23 of body 21 of stem 17 and passes out of hole 39 at second end 25 of stem 17. Stem 17 is thereby guided to the correct position in scaphoid fossa 7 for implantation and then fixated therein by threads 29. Once stem 17 is fixated into radius 1, a reamer is placed over the Kirshner wire. The reamer is used to remove a portion of the articular surface of scaphoid fossa 7 and freshen the bone at scaphoid fossa 7. This portion corresponds to the size and site of articular component 19 of implant 15. The Kirshner wire is then removed and articular component 19 is placed. Articular component 19 is fixedly coupled to stem 17 by inserting post 37 into hole 39 of connection member 27 to form a Morse Taper-Cold Weld fit.

Next, the surgeon must check to ensure top surface 33 of articular component 19 is not proud. In other words, the surgeon must check to ensure that top surface 33 of articular component 19 forms a smooth surface with lunate fossa 9 as shown in FIG. 8. If top surface 33 of articular component 19 is proud, articular component 19 is removed and distal radius 5 is further reamed.

Finally, the surgical area is flushed with irrigation solution, hemostasis is achieved, the dorsal ligaments and capsule are repaired, and the skin is closed. The patient is then placed in a volar slap for approximately one to two weeks. Physical therapy is also started to maintain range of motion at the wrist joint.

Figure 9:
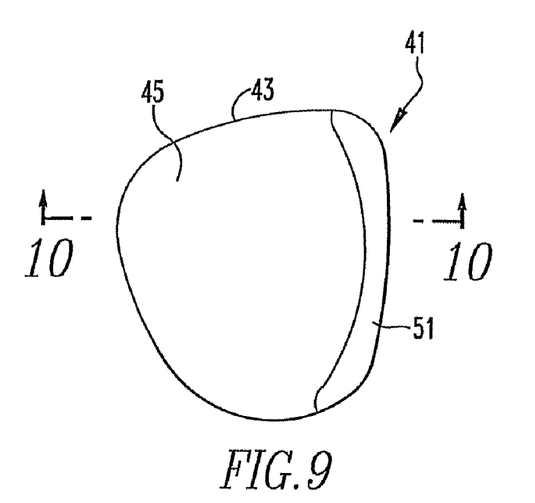
FIG. 9 is a top plan view of an alternative embodiment of the articular component of the modular resurfacing implant in accordance with the present invention.
Figure 10:
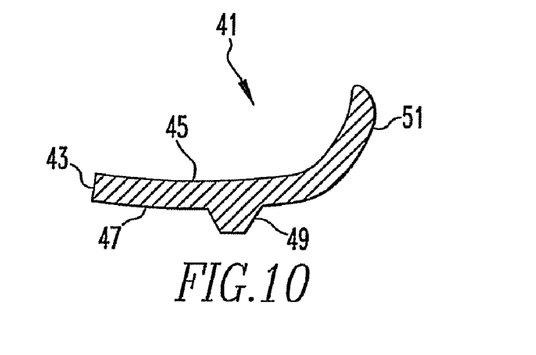
FIG. 10 is a cross-sectional view of the articular component of FIG. 9 taken along line 10-10.

With reference to FIGS. 9 and 10, an alternative embodiment of articular component 41 is illustrated. Articular component 41 includes a body 43 having a top surface 45 and a bottom surface 47. Bottom surface 47 has a post 49 extending therefrom that is configured to mate with hole 39 provided in connection member 27 of body 21 of stem 17. Top surface 45 of articular component 41 is desirably surfaced with a soft metal, such as a cobalt chrome alloy. Bottom surface 47 of articular component 41 may be manufactured from titanium with a roughened surface to encourage osseointegration.

Articular component 41 has generally the same size and shape as articular component 19. However, articular component 41 further includes a dorsal extension 51. Accordingly, articular component 41 is provided to treat patients having a scapholunate ligament injury. Patients with scapholunate ligament injury commonly develop flexion of the scaphoid. This eventually leads to a form of arthritis known as scapholunate advanced collapse (SLAC). Dorsal extension 51 is provided to control scaphoid flexion. More specifically, dorsal extension 51 includes a gradual curve to control the tendency of scaphoid 11 to flex.

Figure 11:
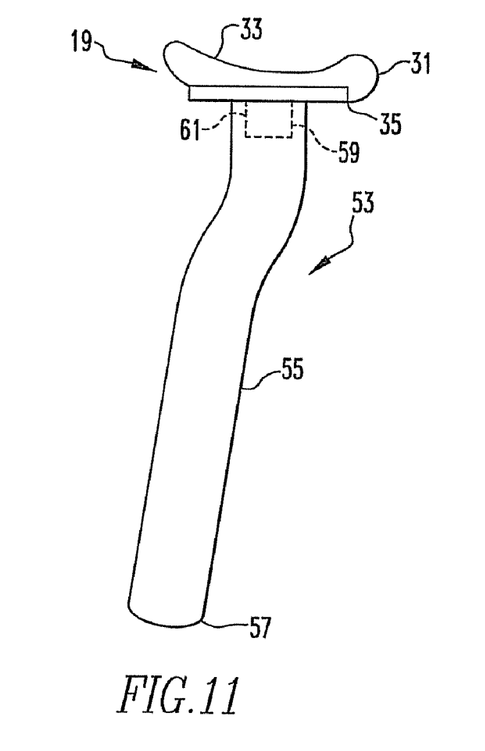
FIG. 11 is side view of another embodiment of the modular resurfacing implant in accordance with the present invention.
Figure 12:
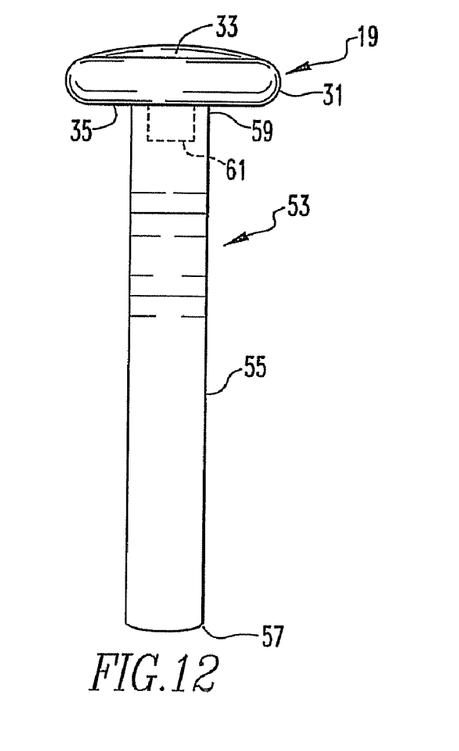
FIG. 12 is a front view of the modular resurfacing implant of FIG. 11.

While the present invention has been described hereinabove as including a threaded stem 17 to provide a screw-fit within radius 1, this is not to be construed as limiting the present invention, as a stem having a press-fit design may also be utilized. With reference to FIGS. 11 and 12, an alternative embodiment of a stem 53 having a press-fit design is illustrated. Stem 53 has an elongated body 55 having a first end 57 and a second end 59. Second end 59 includes a hole 61 for receiving post 37 of articular component 19 or post 49 of articular component 41.

Stem 53 may be provided in a variety of widths and lengths, thereby allowing surgeons to accommodate the various types of patient bone size and density. Desirably, stem 53 is manufactured from titanium with a roughened surface to encourage osseointegration. Finally, stem 53 may be cannulated to allow the surgeon to pass stem 53 over a previously placed guide wire, such as a Kirshner wire. This allows the surgeon to check and optimize the placement of the Kirshner wire. Once the position of the Kirshner wire is confirmed and the site within radius 1 has been prepared by the surgeon, stem 53 can be positioned in scaphoid fossa 7 of distal radius 5 and press-fit within radius 1 using the Kirshner wire as a guide. Thereafter, distal radius 5 is prepared and articular component 19 or 41 is coupled to second end 59 of stem 53 as discussed hereinabove.

While implant 15 has been discussed hereinabove as including modular articular and stem components, this is also not to be construed as limiting the present invention as the articular components and stem components may be provided integrally. In addition, and with reference to FIG. 13, a resurfacing implant 63 may be provided that includes an integrally formed stem 65 and articular component 67. Stem 65 is configured to be press-fit into radius 1 and articular component 67 is configured to resurface scaphoid fossa 7 of distal radius 5 while leaving lunate fossa 9 intact. Stem 65 and articular component 67 may be manufactured from titanium having a roughened surface.

Figure 13:
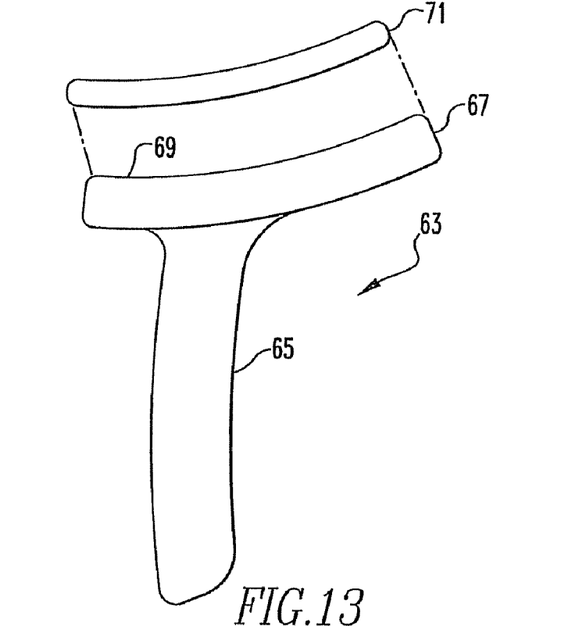
FIG. 13 is a side view of still another embodiment of the modular resurfacing implant in accordance with the present invention.

Articular component 67 is sized and shaped generally the same as articular component 19. However, articular component 67 further includes a tray 69 configured to receive a resurfacing component 71. Resurfacing component 71 is configured to be provided in variable thicknesses to suit a specific patient's needs. Resurfacing component 71 is desirably manufactured from a soft metal, such as a cobalt chrome alloy.

Accordingly, the present invention described hereinabove provides a resurfacing implant for treatment of periscaphoid OA that is provided in two or more modular components that resurfaces the scaphoid fossa of the radius while leaving the lunate fossa of the radius, the distal radioulnar joint, and the ulnocarpal joint intact.

The unicompartmental resurfacing hemiarthroplasty system is beneficially provided for patients with symptomatic periscaphoid OA. Ideal candidates would have OA limited to the scaphoid fossa of the radius. This would include patients with grades 1-2 SLAC or scaphoid non-union advanced collapse (SNAC). However, this is not to be construed as limiting the present invention as the use of a resurfacing implant to resurface only a portion of a joint has also been envisioned. For instance, if the lunate fossa were diseased, an implant could be developed that only replaced the surface of the lunate fossa while leaving the scaphoid fossa intact.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements. For example, it is to be understood that the present invention contemplates that, to the extent possible, one or more features of any embodiment can be combined with one or more features of any other embodiment.

The invention claimed is:

1. A modular resurfacing implant for a radioscaphoid joint of a wrist, the implant comprising:
    a stem comprising a threaded body for implantation into a distal radius and a connection member positioned at a second end of the stem; and
    an articular component comprising a body member configured to resurface a scaphoid fossa of the distal radius, the body member comprising a concave top surface matching a curvature of the scaphoid fossa, a bottom surface having a post extending therefrom that is configured to mate with the connection member of the stem, and a dorsal extension extending from an edge of the concave top surface, the dorsal extension having a gradual curve to control scaphoid flexion,
    wherein the articular component is configured to resurface the scaphoid fossa while leaving a lunate fossa of the distal radius intact.

2. The modular resurfacing implant of claim 1, wherein the articular component is positioned such that it forms a smooth surface with the lunate fossa.

3. The modular resurfacing implant of claim 1, wherein the top surface of the articular component is manufactured from a cobalt chrome alloy.

4. The modular resurfacing implant of claim 1, wherein the bottom surface of the articular component is manufactured from titanium.

5. The modular resurfacing implant of claim 1, wherein the connection member of the stem includes a hole configured to mate with the post of the articular component, thereby fixedly coupling the articular component to the stem.

6. The modular resurfacing implant of claim 1, wherein the stem is cannulated.

7. The modular resurfacing implant of claim 1, wherein the threaded body of the stem tapers from the second end to a first end.

8. The modular resurfacing implant of claim 1, wherein the stem is manufactured from titanium.

9. A resurfacing implant for a radioscaphoid joint of a wrist, the implant comprising:
    a stem comprising an elongated body having a first end and a second end; and
    an articular component comprising a body member extending from the second end of the elongated body of the stem, the articular component comprising a dorsal extension extending from an edge of a top surface thereof, the dorsal extension having a gradual curve to control scaphoid flexion, wherein the elongated body is configured to be implanted into a distal radius of the wrist such that the articular component resurfaces the scaphoid fossa while leaving a lunate fossa of the distal radius intact.

10. The resurfacing implant of claim 9, wherein the stem and the articular component are integrally formed.

11. The resurfacing implant of claim 9, wherein the stem and the articular component are removably coupled.

12. The resurfacing implant of claim 9, wherein the elongated body of the stem is implanted into the distal radius by press-fitting the elongated body into an opening formed in the distal radius.

13. The resurfacing implant of claim 9, wherein the elongated body of the stem is threaded.

14. The resurfacing implant of claim 9, wherein the articular component is positioned such that it forms a smooth surface with the lunate fossa.

15. The resurfacing implant of claim 9, wherein the articular component includes a concave top surface matching a curvature of the scaphoid fossa and a bottom surface.

16. The resurfacing implant of claim 15, wherein the top surface is manufactured from a cobalt chrome alloy.

17. The resurfacing implant of claim 15, wherein the bottom surface is manufactured from titanium.

18. The resurfacing implant of claim 9, wherein the stem is cannulated.

19. The resurfacing implant of claim 9, wherein the elongated body of the stem tapers from the second end to the first end.

* * * * *